(12) United States Patent
Uetsuki

(10) Patent No.: US 11,406,804 B2
(45) Date of Patent: Aug. 9, 2022

(54) LIQUID MEDICINE SUPPLY DEVICE

(71) Applicant: KOBAYASHI PHARMACEUTICAL CO., LTD., Osaka (JP)

(72) Inventor: Hidetomo Uetsuki, Osaka (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 329 days.

(21) Appl. No.: 16/495,073

(22) PCT Filed: Mar. 22, 2018

(86) PCT No.: PCT/JP2018/011408
§ 371 (c)(1),
(2) Date: Sep. 17, 2019

(87) PCT Pub. No.: WO2018/174160
PCT Pub. Date: Sep. 27, 2018

(65) Prior Publication Data
US 2020/0086098 A1  Mar. 19, 2020

(30) Foreign Application Priority Data

Mar. 23, 2017  (JP) .............................. JP2017-057605

(51) Int. Cl.
*A61M 35/00* (2006.01)
*B65D 50/00* (2006.01)
(Continued)

(52) U.S. Cl.
CPC ........... *A61M 35/003* (2013.01); *B65D 41/04* (2013.01); *B65D 50/00* (2013.01); *B65D 50/04* (2013.01);
(Continued)

(58) Field of Classification Search
CPC . A61J 1/1418; B65D 50/041; B65D 2215/02; A61M 35/003
(Continued)

(56) References Cited

U.S. PATENT DOCUMENTS 3,795,338 A * 3/1974 Swartzbaugh ....... B65D 50/041
 215/220
3,857,505 A   12/1974 Mumford
(Continued)

FOREIGN PATENT DOCUMENTS

JP  1983-011660 A  1/1983
JP  S58-000956 U  1/1983
(Continued)

OTHER PUBLICATIONS

Office Action of Japanese Patent Application No. 2017-057605: Notice of Reasons for Refusal dated May 12, 2021 (4 sheets, 4 sheets translation, 8 sheets total).
(Continued)

*Primary Examiner* — James N Smalley
(74) *Attorney, Agent, or Firm* — Kratz, Quintos & Hanson, LLP

(57) ABSTRACT

A medical liquid supply device that includes: a container including a containing portion with a mouth (16); an interior cap (30); and an exterior cap (60). The interior and exterior caps (30, 60) include a ratchet mechanism (50, 80). The interior cap (30) includes: an interior-cap main body (32) and an interior-cap protrusion (54). The interior-cap main body (32) includes a contact ring (44). The exterior cap (60) includes: an exterior-cap main body (62); and an exterior-cap protrusion (84) configured to be engaged with the interior-cap protrusion (54). The contact ring (44) is distant from the interior-cap protrusion (54) in the radial direction of the interior-cap main body (32).

15 Claims, 12 Drawing Sheets

(51) Int. Cl.
  *B65D 41/04*   (2006.01)
  *B65D 50/04*   (2006.01)
(52) U.S. Cl.
  CPC ........ *B65D 50/041* (2013.01); *B65D 2215/00* (2013.01); *B65D 2215/02* (2013.01)
(58) Field of Classification Search
  USPC ........................................................ 215/220
  See application file for complete search history.

(56) References Cited

U.S. PATENT DOCUMENTS

| | | | |
|---|---|---|---|
| 4,410,098 A | 10/1983 | Dubs et al. | |
| 4,523,688 A * | 6/1985 | Puresevic | B65D 50/041 |
| | | | 215/220 |
| 5,370,251 A * | 12/1994 | Buono | B65D 50/041 |
| | | | 215/220 |
| 6,085,920 A | 7/2000 | Moretti | |
| 8,316,622 B2 * | 11/2012 | Jajoo | B65D 50/041 |
| 2014/0014611 A1 | 1/2014 | Buehler et al. | |
| 2016/0167838 A1 * | 6/2016 | Dong | B65D 50/041 |
| | | | 220/255 |
| 2019/0076633 A1 * | 3/2019 | Kanesaka | A61M 35/003 |

FOREIGN PATENT DOCUMENTS

| | | |
|---|---|---|
| JP | S59-012541 B2 | 3/1984 |
| JP | S59-106855 U | 7/1984 |
| JP | H02-001656 U | 1/1990 |
| JP | H08-34454 A | 2/1996 |
| JP | H08-217104 A | 8/1996 |
| JP | 2001-301783 A | 10/2001 |
| JP | 2015-527268 A | 9/2015 |
| JP | 2015-231848 A | 12/2015 |
| WO | 2017/003953 A2 | 1/2017 |

OTHER PUBLICATIONS

International Search Report for International Application No. PCT/JP2018/011408 dated Jun. 12, 2018 (3 sheets, 2 sheets translation, 5 sheets total).

* cited by examiner

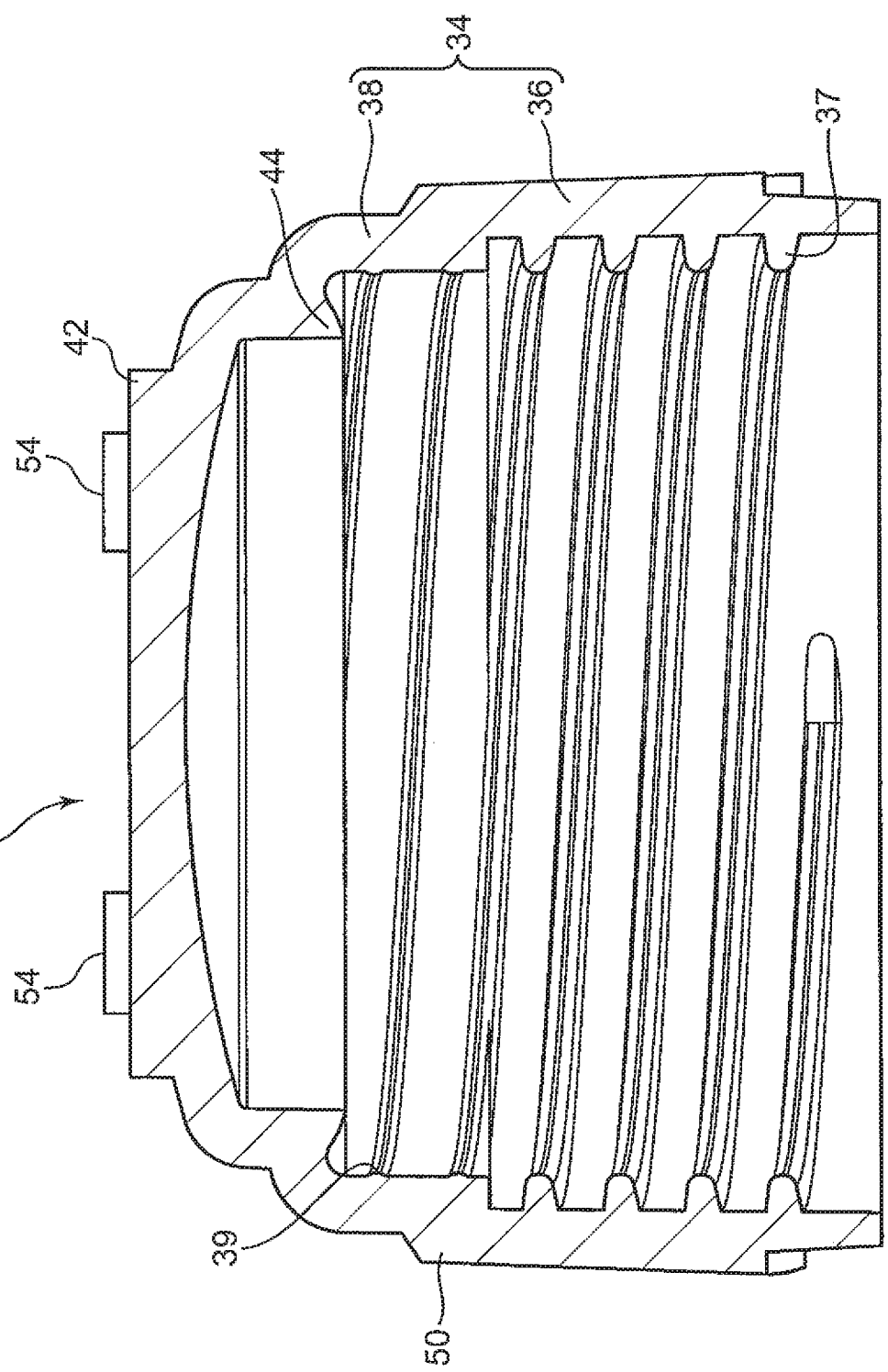

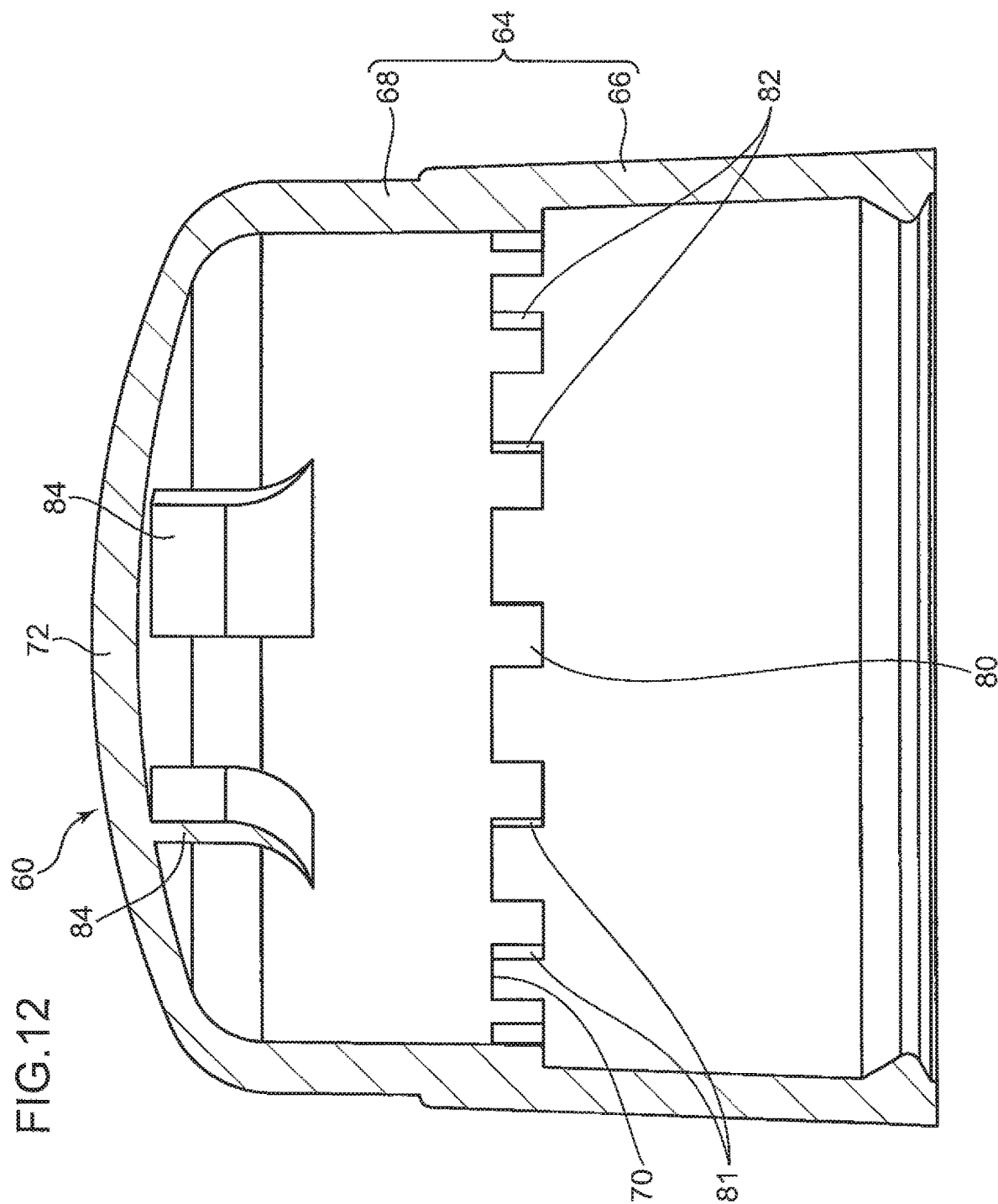

LIQUID MEDICINE SUPPLY DEVICE

TECHNICAL FIELD

The present invention relates to a medical liquid supply device configured to supply a medical liquid to a supplied part such as the skin.

BACKGROUND ART

It has been conventionally known that medical liquid supply devices for supplying a medical liquid to a supplied part and medical liquid containing devices for containing a medical liquid have child resistant mechanisms (child-proof mechanisms) to prevent infants and children from accidentally opening the medical liquid supply devices and the medical liquid containing devices. For example, Patent Literature 1 discloses a containing device including a tubular container, an inner cap member configured to be screwed into a cylindrical mouth of the container, an outer cap member configured to cover the inner cap member, and a seal disk between the inner cap member and the mouth, the seal disk being configured to tightly seal the container. The inner and outer cap members include a ratchet mechanism as the child resistant mechanism. The ratchet mechanism is engaged and disengaged. In detail, drive members are arranged on the circumferential edge of the top plate of the inner cap member at regular intervals in the circumferential direction of the top plate of the inner cap member. Drive protrusions are arranged on the circumferential edge of the bottom surface of the top plate of the outer cap member at regular intervals in the circumferential direction of the top plate of the outer cap member. The drive protrusions are configured to engage with the drive members. The drive protrusions are engaged with the drive members with pressing the outer cap member against the inner cap member.

Leaf spring members extend from the inner surface of the top plate of the outer cap member. The leaf spring members urge the top plate of the outer cap member away from the inner cap member. Ratchet protrusions extend from the upper surface of the top plate of the inner cap member. The ratchet protrusions are configured to engage with the lower ends of the leaf spring members. The leaf spring members extend from the top plate of the outer cap member to the top plate of the inner cap member. The leaf spring members elastically deform. When the outer cap member is rotated relative to the inner cap member in a tightening direction, a shape of each of the ratchet protrusions allows the ratchet protrusions to engage with the leaf spring members. Alternatively, when the outer cap member is rotated relative to the inner cap member in an untightening direction, the shape of each of the ratchet protrusions allows the leaf spring members to slip over the ratchet protrusions.

Even when the outer cap member of the containing device without being pressed against the inner cap member of the containing device (disengagement of the drive protrusions from the drive members) is rotated relative to the mouth of the container in the untightening direction, the outer cap member is rotated relative to the inner cap member. Therefore, the outer and inner cap members are not removed from the container (unopened). At this time, the leaf spring members deform elastically and slip over the ratchet protrusions. On the other hand, the outer cap member pressed to the inner cap member against an urging force of the leaf spring members (engagement of the drive protrusions with the drive members) is rotated relative to the mouth of the container. Consequently, the outer and inner cap members are integrally rotated relative to the mouth of the container. Therefore, the outer and inner cap members are removed from the container (opened). When the outer cap member is rotated in the tightening direction in order to attach the outer and inner cap members to the container, the lower ends of the leaf spring members presses the ratchet protrusions of the inner cap member even without the outer cap member pressed against the inner cap member. Consequently, the outer and inner cap members are integrally rotated relative to the mouth, and eventually the outer and inner cap members are attached to the container.

CITATION LIST

Patent Literature

Patent Literature 1: JP S59-12541 B

SUMMARY OF INVENTION

Problems to be Solved by the Invention

Such a containing device as described in Patent Literature 1 includes many parts since the containing device includes a seal disk configured to prevent leakage of contents (e.g. medical liquid) from the container. Likewise, this may be in common to a medical liquid supply device for supplying medical liquid.

It is an object of the present invention to provide a medical liquid supply device with a reduced number of parts, the medical liquid supply device being configured to prevent infants and children from accidentally opening the medical liquid supply device.

Solutions to the Problems

In order to overcome the aforementioned problems, it is considered that a contact ring is attached to an interior cap. The contact ring comes into contact with a top surface of a mouth of a container or a top surface of a stopper to tightly seal the container. Consequently, it is not required that a sealing member seals the container between the mouth of the container and the interior cap. However, if ratchet protrusions on an interior-cap side and the contact ring overlap in the axial direction of the interior cap, sink marks may happen to the contact ring when synthetic resin is shaped into the interior cap in a mold (a risk of insufficient seal for the container).

A medical liquid supply device according to an aspect of the present invention includes: a container including a tubular containing portion for containing a liquid medicine, and a cylindrical mouth connected to the containing portion, the mouth including a male thread; an interior cap including a female thread with which the male thread of the mouth is engaged, the interior cap being made of synthetic resin to have a shape operable to block an opening of the mouth; and an exterior cap attached to an outside of the interior cap. The interior and exterior caps include a ratchet mechanism configured to be engaged and disengaged. The ratchet mechanism is configured to allow an integral rotation of the exterior and interior caps when the exterior cap is rotated in a direction to remove the exterior cap from the mouth under a condition of the exterior cap pressed against the interior cap whereas the ratchet mechanism allows the exterior cap to be rotated relative to the interior cap when the exterior cap is rotated in a direction to remove the exterior cap from the mouth under a condition of the exterior cap which is not pressed against the interior cap so that the exterior cap is separated from the interior cap. The interior cap includes: an interior-cap main body including the female thread, the interior-cap main body having a shape operable to block the opening of the mouth; and an interior-cap protrusion protruding from an outer surface of the interior-cap main body to the exterior cap. The interior-cap main body includes a contact ring which is annular around a central axis of the interior-cap main body, the contact ring coming into contact with the mouth or a stopper attached to the mouth to tightly close the container. The exterior cap includes: an exterior-cap main body having a shape operable to cover the interior-cap main body; and an exterior-cap protrusion protruding from an inner surface of the exterior-cap main body to the interior-cap main body, the exterior-cap protrusion having a shape operable to be engaged with the interior-cap protrusion. One of the interior-cap protrusion and the exterior-cap protrusion urges the exterior-cap main body away from the interior-cap main body to disengage the ratchet mechanism under an unpressed state of the exterior-cap main body which is not pressed against the interior-cap main body. One of the interior-cap protrusion and the exterior-cap protrusion engages with the other of the interior-cap protrusion and the exterior-cap protrusion to allow the integral rotation of the interior-cap main body and the exterior-cap main body when the exterior-cap main body is rotated in a direction to close the mouth with the exterior-cap main body under the unpressed state. One of the interior-cap protrusion and the exterior-cap protrusion elastically deforms and slides over the other protrusion when the exterior-cap main body is rotated in a direction to remove the exterior-cap main body from the mouth under the unpressed state. The contact ring is distant from the interior-cap protrusion in a radial direction of the interior-cap main body.

According to the aforementioned medical liquid supply device, the contact ring is distant from the interior-cap protrusion in the radial direction of the interior-cap main body. Therefore, the interior-cap protrusion does not cause sink marks on the contact ring when synthetic resin is shaped into the interior cap in a mold. Therefore, the medical liquid supply device configured to prevent infants and children from accidentally opening the medical liquid supply device requires a reduced number of parts to seal the container.

With regard to the aforementioned configuration, preferably, the exterior-cap protrusion may form the one protrusion, the exterior-cap protrusion including spring pieces which extend from the exterior-cap main body to the interior-cap main body, and elastically deform and bend in a direction so that the spring pieces connect the exterior-cap main body with the interior-cap main body. The interior-cap protrusion may form the other protrusion, the interior-cap protrusion including ribs, each of which has a shape operable to be engaged with lower ends of the spring pieces. The ribs may include: receiving portions configured to receive the spring pieces, respectively when the exterior-cap main body is rotated in a direction to close the mouth with the exterior-cap main body under the unpressed state; and guiding portions configured to guide the spring pieces, respectively to allow the spring pieces to elastically deform and slide over the ribs when the exterior-cap main body is rotated in a direction to remove the exterior-cap main body from the mouth under the unpressed state.

According to the aforementioned configuration, it becomes easy to manufacture the interior cap. In detail, the interior cap includes the female thread. Therefore, when synthetic resin is shaped into the interior cap in a mold, the interior cap has to be rotated to be removed from the mold. Therefore, it becomes easier to remove the interior cap from a mold when the interior cap includes the interior-cap protrusion which forms the ribs than another interior cap including interior-cap protrusions which form spring pieces.

With regard to the aforementioned configuration, preferably, the interior-cap main body may include: an interior-cap circular wall including the female thread; and an interior-cap upper wall connected to an upper end of the interior-cap circular wall, the interior-cap upper wall being configured to support the contact ring.

A top surface of the interior-cap upper wall may be curved so that the top surface protrudes toward the exterior-cap main body in an axial direction of the interior-cap circular wall.

According to the aforementioned configuration, there is a low risk of weakening engagement with time between the spring pieces and the ribs. In detail, since the top surface of the interior-cap upper wall is curved to be convex toward the exterior-cap main body, it is less likely that the interior-cap upper wall deforms to inwardly dent because of an inward load continuously acting along the axial direction of the interior-cap circular wall, the inward load being transmitted to the interior-cap upper wall through the spring pieces. It is also less likely that the engagement becomes weak with time between the spring pieces and the ribs.

Alternatively, the interior-cap upper wall may have a top surface inside the contact ring, the top surface perpendicularly intersecting an axial direction of the interior-cap circular wall. The interior-cap upper wall may have a bottom surface inside the contact ring, the bottom surface being curved to be convex toward the exterior-cap main body in the axial direction of the interior-cap circular wall.

According to the aforementioned configuration, the interior-cap upper wall may be thick enough inside the contact ring to suppress sink marks on the contact ring when synthetic resin is shaped into the interior cap in a mold. It is less likely that the interior-cap upper wall deforms to inwardly dent under an inward load of the spring pieces on the interior-cap upper wall. It is also less likely that the engagement becomes weak with time between the spring pieces and the ribs.

With regard to the aforementioned configuration, the interior cap may further include engaging portions on the outer surface of the interior-cap main body. The exterior cap may further include engaged portions on the inner surface of the exterior-cap main body, each of the engaged portions having a shape operable to be engaged with each of the engaging portions. The engaged portions and the engaging portions may constitute the ratchet mechanism. The contact ring may be distant from the engaging portions in the radial direction of the interior-cap main body.

According to the aforementioned configuration, the engaging portions do not cause sink marks on the contact ring when synthetic resin is shaped into the interior cap in a mold.

With regard to the aforementioned medical liquid supply device, preferably, the spring pieces may be spirally formed.

According to the aforementioned configuration, there are lower stresses at proximal ends of the spring pieces when the spring pieces are spirally formed than when the spring pieces are radially formed.

With regard to the aforementioned medical liquid supply device, preferably, each of ribs may be formed on a portion at which each of the ribs overlaps with a circle connecting proximal ends of the spring pieces in a direction connecting the exterior-cap main body with the interior-cap main body.

According to the aforementioned configuration, a force is efficiently transmitted from the exterior-cap main body to the interior-cap main body through the spring pieces and the ribs. Therefore, it is less likely that the spring pieces are broken by a resistant force which the spring pieces receive from the ribs.

Advantageous Effect of the Invention

As described above, a medical liquid supply device according to an aspect of the present invention is provided with a reduced number of parts, the medical liquid supply device being configured to prevent infants and children from accidentally opening the medical liquid supply device.

BRIEF DESCRIPTION OF DRAWINGS

FIG. 11 is a cross-sectional view of an example of variation of the interior cap.

FIG. 12 is a cross-sectional view of an example of variation of the exterior cap.

DESCRIPTION OF EMBODIMENT

A medical liquid supply device 1 according to an embodiment of the present invention is described with reference to FIGS. 1 to 10. The medical liquid supply device 1 supplies a medical liquid to a supplied part such as the skin. The medical liquid supply device 1 includes what is called a child resistant mechanism (child-proof mechanism) configured to prevent infants and children from accidentally opening the medical liquid supply device 1. The medical liquid supply device 1 is not limited by a direction at a time of usage. However, the vertical direction is defined on the basis of the vertical direction in FIG. 1, for convenience.

Figure 1:
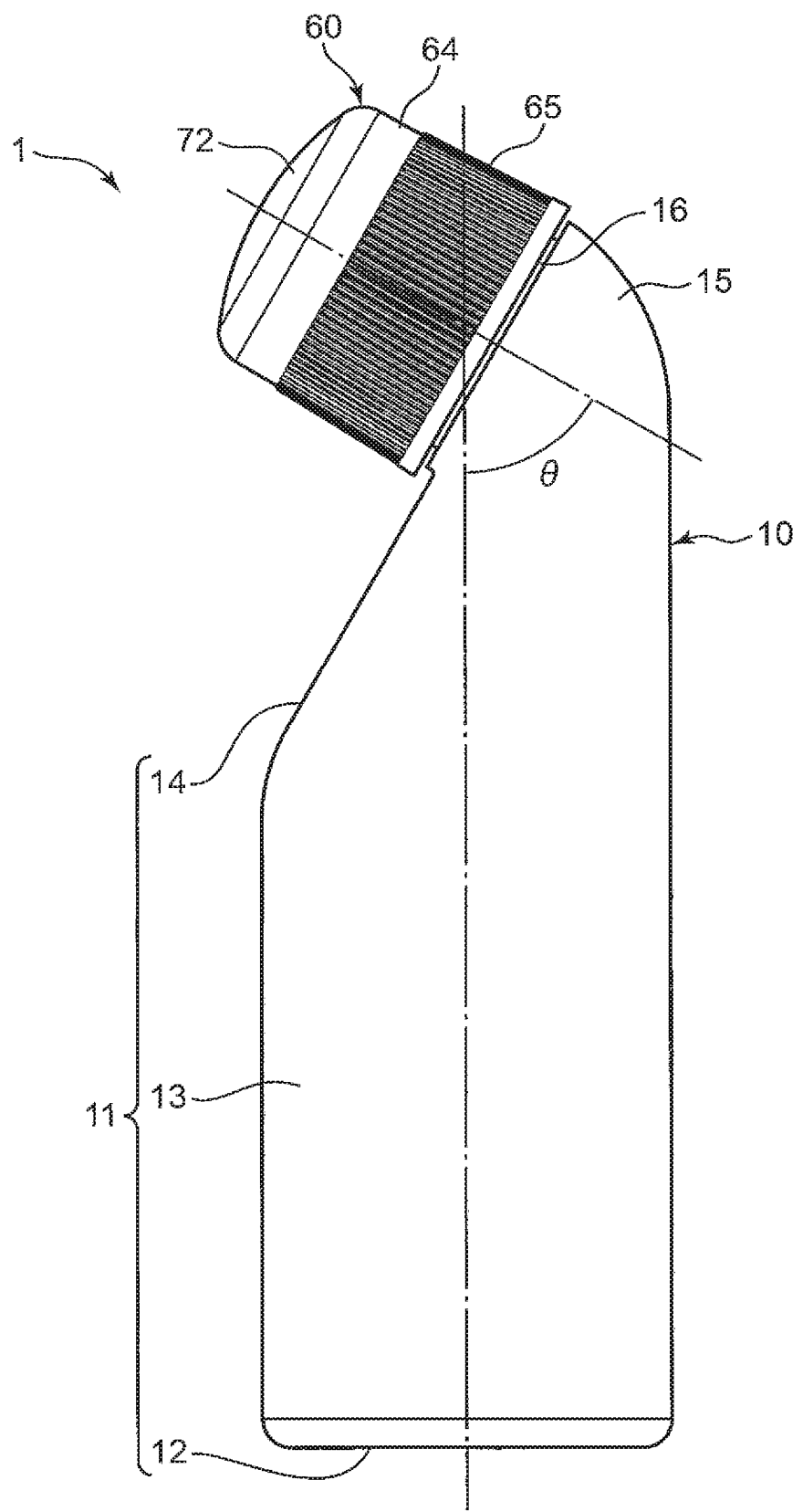
FIG. 1 is a front view of a medical liquid supply device according to an embodiment of the present invention.
Figure 4:
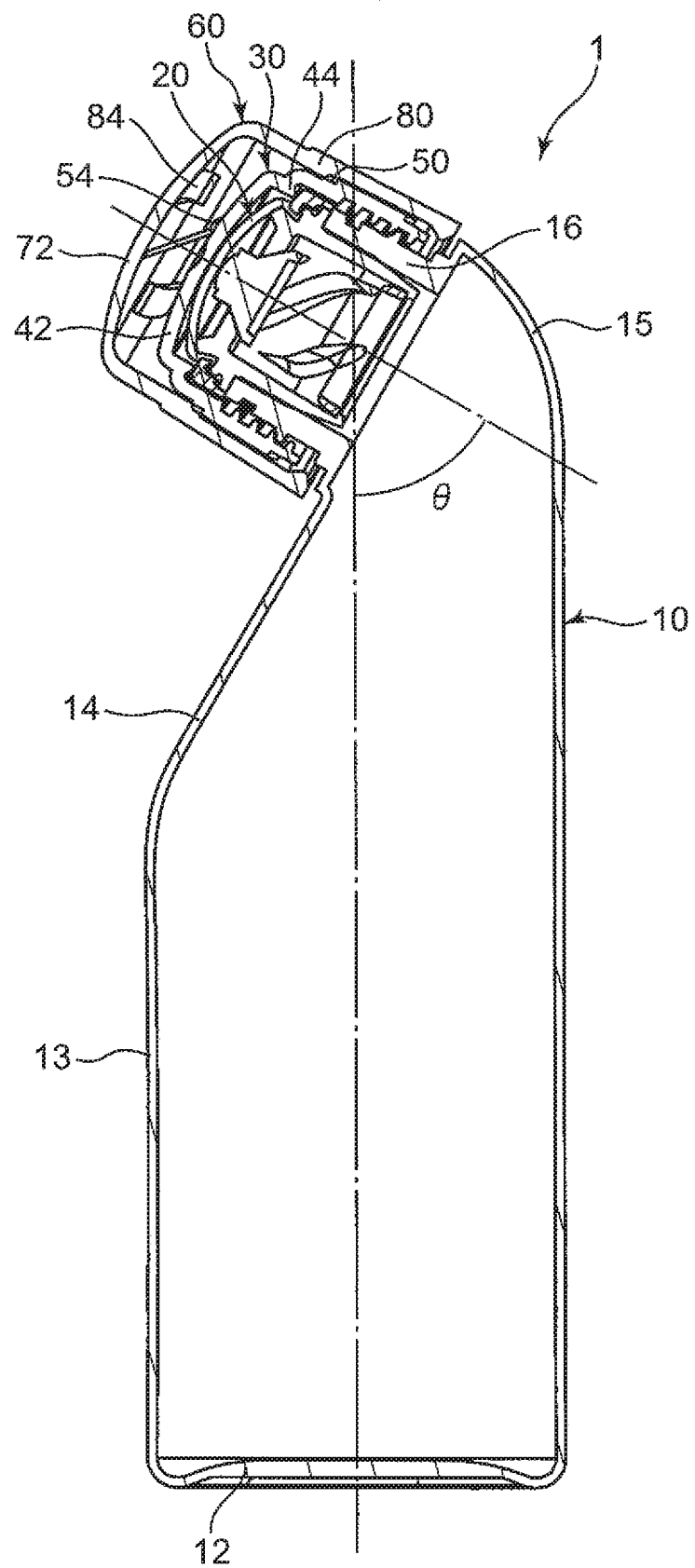
FIG. 4 is a cross-sectional view of the medical liquid supply device in FIG. 1.
Figure 5:
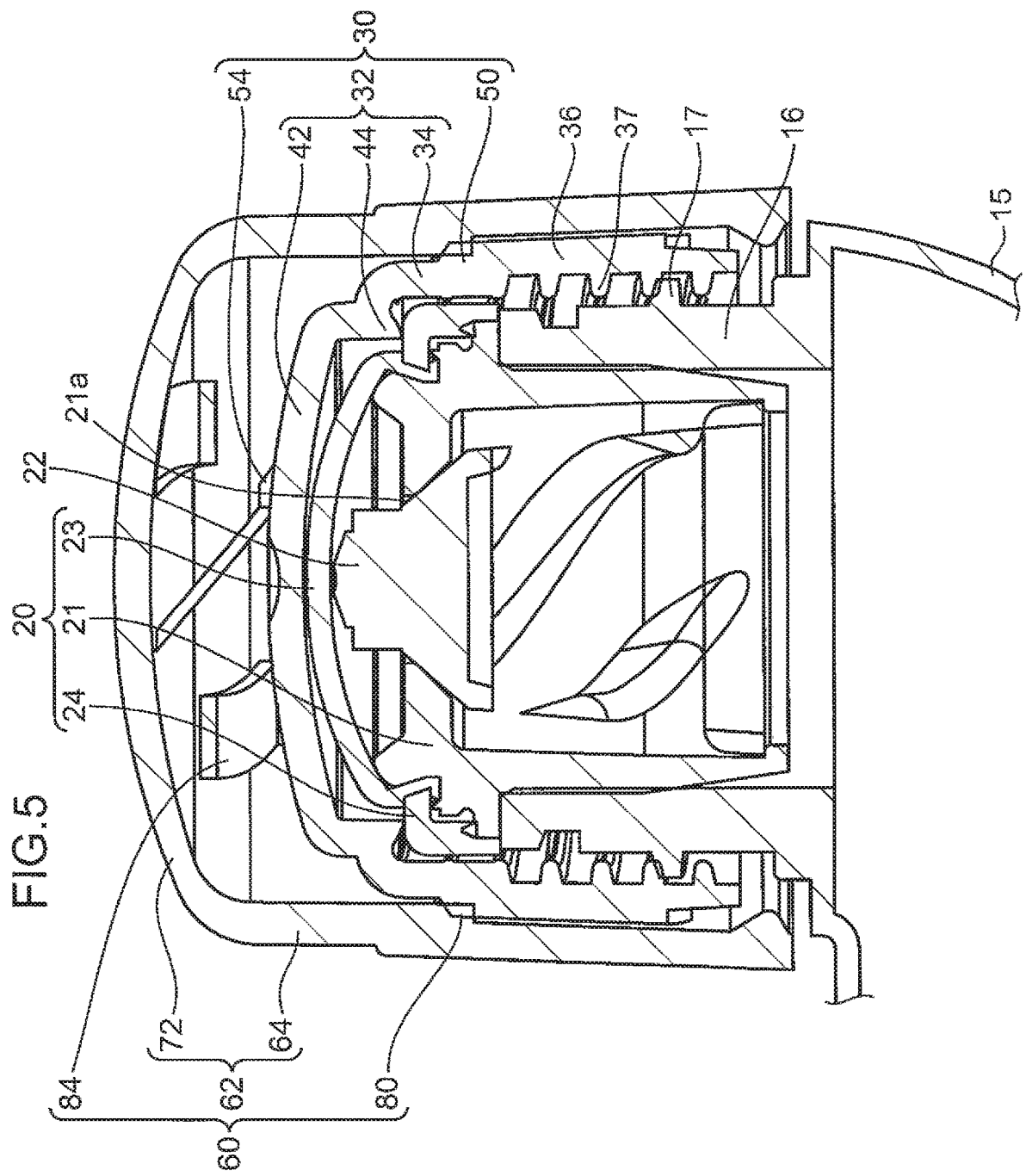
FIG. 5 is an enlarged view of a mouth, an interior cap and an exterior cap in FIG. 4.

As shown in FIGS. 1, 4 and 5, for example, the medical liquid supply device 1 includes a container 10, a stopper 20, an interior cap 30 and an exterior cap 60. The interior and exterior caps 30, 60 include a ratchet mechanism as the child resistant function. The ratchet mechanism is engaged and disengaged. The ratchet mechanism is engaged under a condition of the exterior cap 60 pressed against the interior cap 30, so that the ratchet mechanism allows an integral rotation of the exterior and interior caps 60, 30 when the exterior cap 60 is rotated. The ratchet mechanism is disengaged under a condition of the exterior cap 60 which is not pressed against the interior cap 30, so that the ratchet mechanism allows the exterior cap 60 to be rotated relative to the interior cap 30 (idling) when the exterior cap 60 is rotated. The ratchet mechanism is described in detail below.

The container 10 includes a containing portion 11, a neck 15 and a mouth 16.

The containing portion 11 contains a medical liquid. In detail, the containing portion 11 includes a bottom wall 12, a body 13 and a contractive portion 14.

Figure 3:
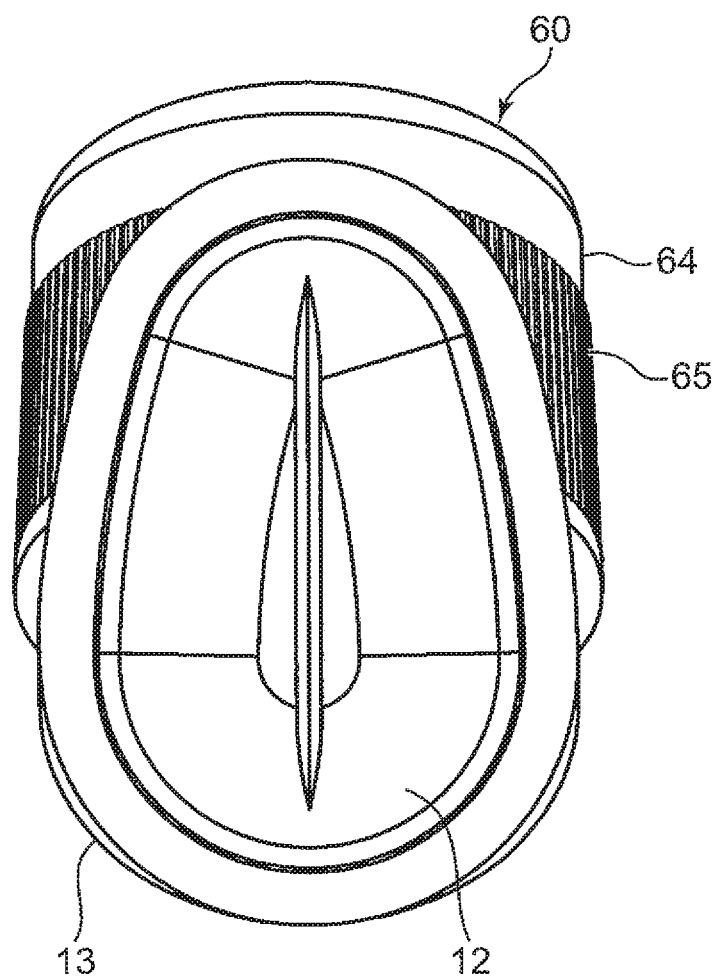
FIG. 3 is a bottom view of the medical liquid supply device in FIG. 1.

The body 13 extends upward from an edge of the bottom wall 12. The body 13 is tubular. As shown in FIGS. 1 and 3, the body 13 is longer in length in first directions (vertical direction in FIG. 3) perpendicularly intersecting the axial direction of the body 13 than second directions (lateral direction in FIG. 3) perpendicularly intersecting both the axial direction and the first direction of the body 13.

The contractive portion 14 is connected to the upper end of the body 13. A diameter of the contractive portion 14 becomes gradually smaller from the body 13 to the upper end of the contractive portion 14.

The neck 15 is connected to the upper end of the contractive portion 14.

Figure 2:
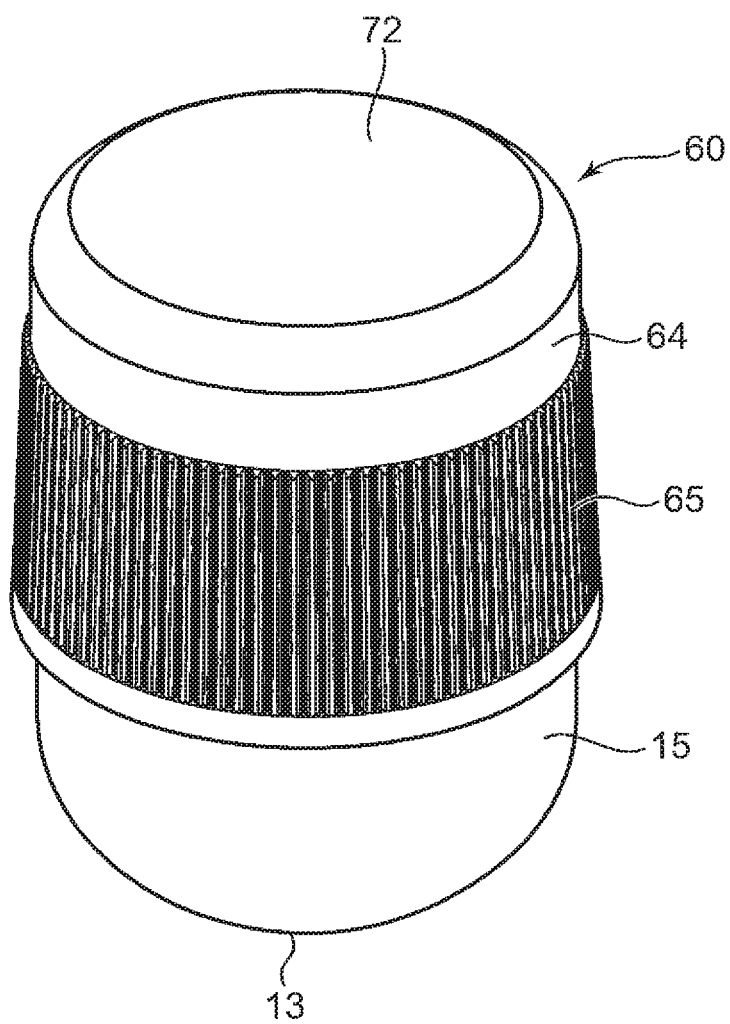
FIG. 2 is a plan view of the medical liquid supply device in FIG. 1.

The mouth 16 is connected to the upper end of the neck 15. The mouth 16 is cylindrical. The mouth 16 includes a male thread 17. As shown in FIGS. 1 and 4, the central axis of the mouth 16 is inclined from the central axis of the containing portion 11 by a predetermined angle θ. With regard to the present embodiment, the predetermined angle θ is 60°. In order to prevent infants and children from accidentally opening the medical liquid supply device 1, the predetermined angle θ is preferably 15° to 75°. As shown in FIG. 2, a projected line of the axial direction of the mouth 16 is in parallel to the first direction when the line is projected on a projection plane from a plan view of the container 10.

The stopper 20 is attached to the mouth 16. The stopper 20 includes a stopper main body 21 pressed into the mouth 16, a sponge 23 made of polyurethane to cover the stopper main body 21, and a sandwiching portion 24. The sponge 23 is sandwiched between the sandwiching portion 24 and the stopper main body 21. The stopper main body 21 includes an urging portion 22 configured to urge the sponge 23 against an interior-cap upper wall of the interior cap 30 (leftward in FIG. 5). The urging portion 22 is configured to block a medical liquid outlet 21a of the stopper main body 21. An edge of the sponge 23 is sandwiched between the sandwiching portion 24 and the stopper main body 21. When the medical liquid supply device 1 is used (under a removal condition of the interior and exterior caps 30, 60), the sponge 23 and the urging portion 22 are pressed against an urging force of the urging portion 22 under a condition of the sponge 23 in contact with the supplied part. Consequently, the medical liquid flows through the medical liquid outlet 21a. The sponge 23 absorbs the medical liquid flown through the medical liquid outlet 21a to supply the medical liquid onto a supplied part.

Next, the interior cap 30 is described with reference to FIGS. 5 to 7. The interior cap 30 is removably connected to the mouth 16. The interior cap 30 is connected to the mouth 16 to tightly seal the container 10. The interior cap 30 is made of synthetic resin. The interior cap 30 includes an interior-cap main body 32, engaging portions 50 to constitute a part of the ratchet mechanism on an outer surface of the interior-cap main body 32, and ribs 54 on the outer surface of the interior-cap main body 32, the ribs 54 being used as the exterior-cap protrusions.

The interior-cap main body 32 includes a female thread 37 with which the male thread 17 engages. The interior-cap main body 32 is configured to block the opening of the mouth 16. In detail, the interior-cap main body 32 includes an interior-cap circular wall 34 having the female thread 37, an interior-cap upper wall 42 and a contact ring 44.

The interior-cap circular wall 34 includes a cylindrical large-outer-diameter portion 36, and a small-outer-diameter portion 38 which is smaller in outer diameter than the large-outer-diameter portion 36. The female thread 37 is on an inner curved surface of the large-outer-diameter portion 36.

The small-outer-diameter portion 38 is connected to the upper end of the large-outer-diameter portion 36. As shown in FIGS. 6 and 8, the outer surface of the interior-cap circular wall 34 includes an inner arrangement surface 40 at the boundary between the large-outer-diameter portion 36 and the small-outer-diameter portion 38. The inner arrangement surface 40 perpendicularly intersects the axial direction of the interior-cap circular wall 34. As shown in FIG. 7, the inner surface of the small-outer-diameter portion 38 may include a small female thread 39. The small female thread 39 is not engaged with the male thread 17 of the mouth 16. With regard to the present embodiment, a projection amount of the female thread 37 from the inner surface of the large-outer-diameter portion 36 is 0.95 mm. On the other hand, a projection dimension of the small female thread 39 from the inner surface of the small-outer-diameter portion 38 is approximately 0.1 mm.

The interior-cap upper wall 42 is connected to the upper end of the interior-cap circular wall 34. The interior-cap upper wall 42 has a shape like a disk. The top and bottom surfaces of the interior-cap upper wall 42 are curved to be convex outward (leftward in FIGS. 6 and 7) in the axial direction of the interior-cap circular wall 34.

The contact ring 44 protrudes inward (rightward in FIG. 7) from the bottom surface (inner surface) of the interior-cap upper wall 42. The contact ring 44 is annular around the central axis of the interior-cap upper wall 42. As shown in FIG. 5, when the female thread 37 is engaged with the male thread 17, the contact ring 44 comes into contact with the top surface of the sandwiching portion 24 of the stopper 20 to tightly seal the container 10.

The engaging portions 50 are on the inner arrangement surface 40. The engaging portions 50 protrude from the inner arrangement surface 40 to the exterior cap 60 (leftward in FIG. 6). The engaging portions 50 are arranged at regular intervals in the circumferential direction of the interior-cap circular wall 34.

Figure 7:
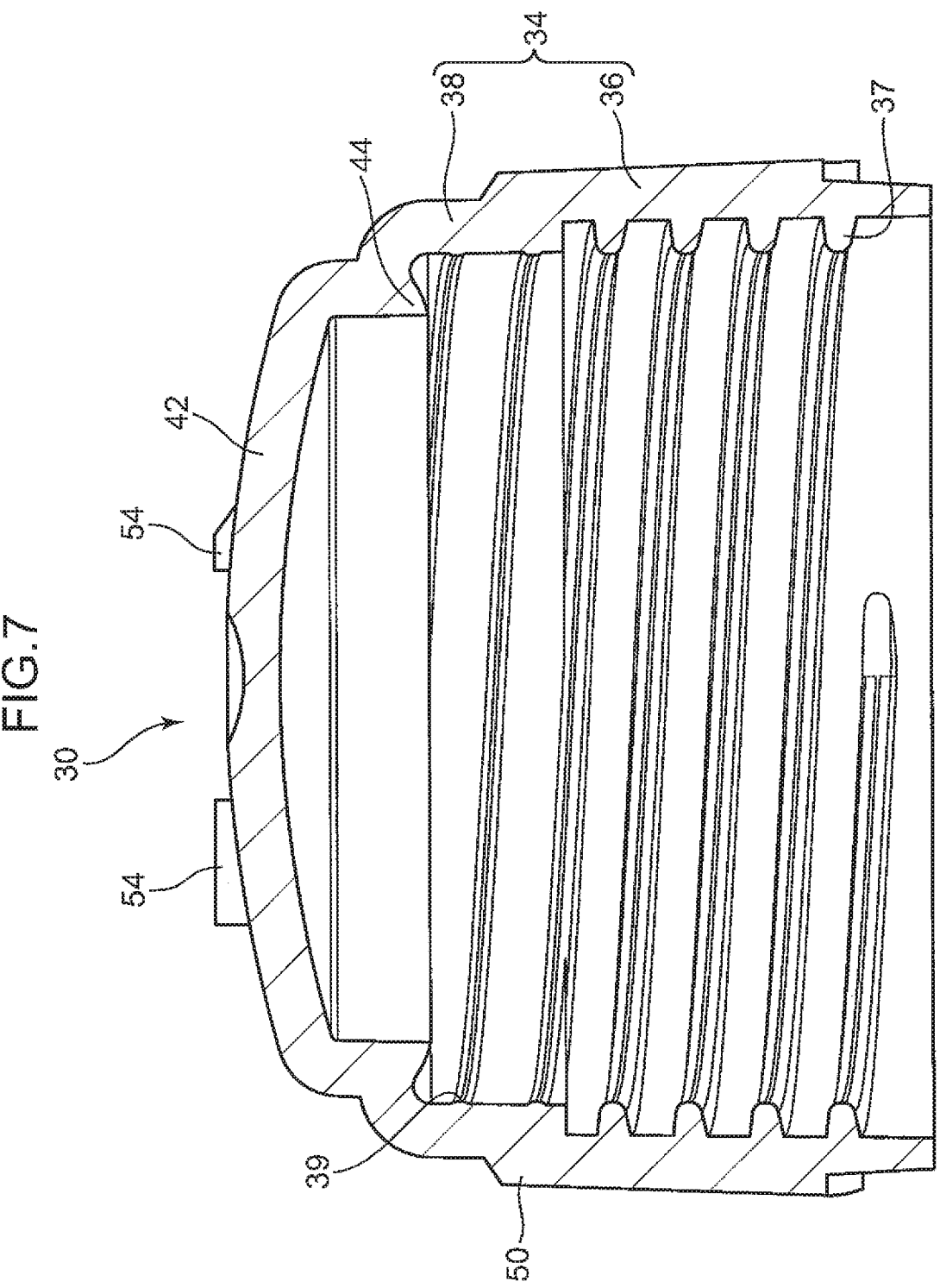
FIG. 7 is a cross-sectional view taken along line VII-VII in FIG. 6.
Figure 8:
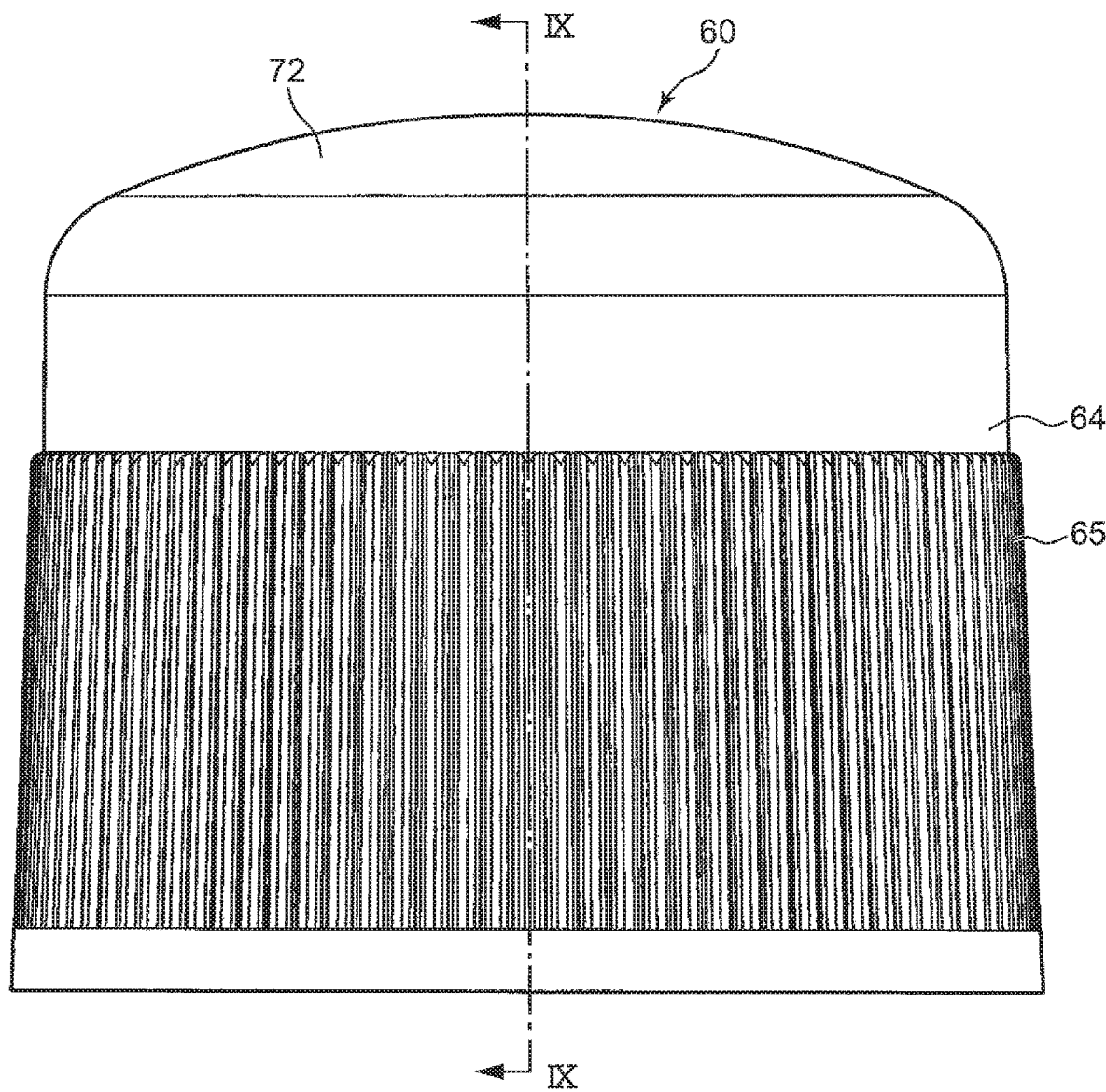
FIG. 8 is a front view of the exterior cap.

As shown in FIGS. 5 and 7, the engaging portions 50 are distant from the contact ring 44 in the radial direction of the interior-cap circular wall 34. The engaging portions 50 are also distant from the female thread 37 in the axial direction of the interior-cap circular wall 34. In detail, the engaging portions 50 are between the contact ring 44 and the female thread 37 in the axial direction of the interior-cap circular wall 34. The engaging portions 50 are on the inner arrangement surface 40 outside the contact ring 44 in the radial direction of the interior-cap circular wall 34.

Figure 6:
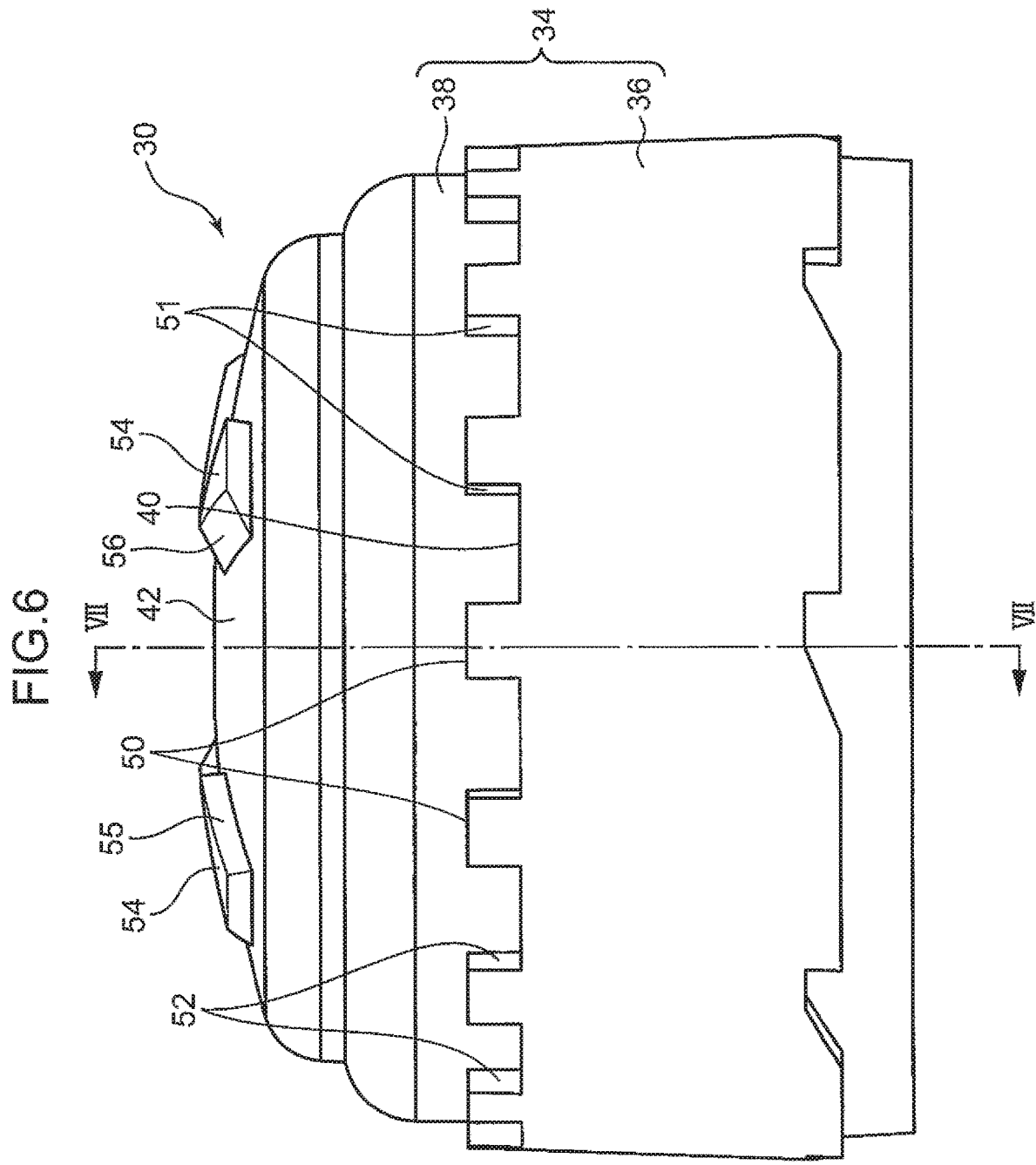
FIG. 6 is a front view of the interior cap.

As shown in FIG. 6, each of the engaging portions 50 includes an open-time-pressed-surface 51 and a close-time-pressed-surface 52. These are described below.

The ribs 54 protrude upward from the top surface of the interior-cap upper wall 42. The ribs 54 (four in the present embodiment) are arranged at regular intervals to be annular around the central axis of the interior-cap circular wall 34. As shown in FIG. 7, the ribs 54 are inside the contact ring 44 in the radial direction of the interior-cap circular wall 34. Functions of the ribs 54 are described below.

Figure 9:
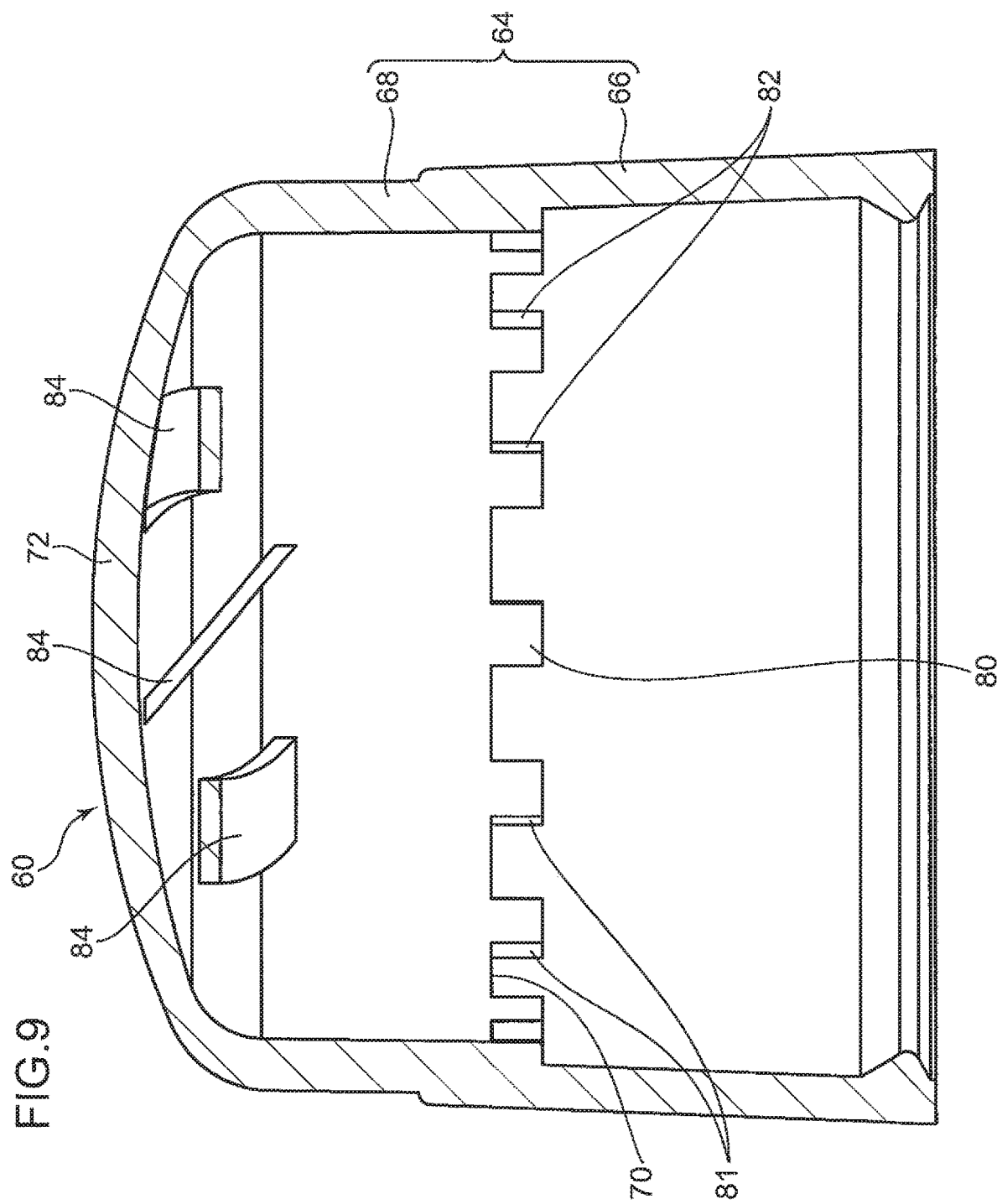
FIG. 9 is a cross-sectional view taken along line IX-IX in FIG. 8.

The exterior cap 60 is described with reference to FIGS. 5, 8 and 9. The exterior cap 60 is attached to the outside of the interior cap 30. The exterior cap 60 is movable relative to the interior cap 30 in the axial direction of the interior cap 30. The exterior cap 60 is made of synthetic resin. The exterior cap 60 includes an exterior-cap main body 62, and engaged portions 80 on the inner surface of the exterior-cap main body 62. The engaged portions 80 and the engaging portions 50 constitute the ratchet mechanism. The exterior cap 60 also includes spring pieces 84 configured to be engaged with the ribs 54, the exterior cap 60 being used as the exterior-cap protrusions.

The exterior-cap main body 62 is configured to cover the interior-cap main body 32. The exterior-cap main body 62 includes an exterior-cap circular wall 64 and an exterior-cap upper wall 72.

The exterior-cap circular wall 64 includes a cylindrical large-inner-diameter portion 66, and a small-inner-diameter portion 68 which is smaller in inner diameter than the large-inner-diameter portion 66. As shown in FIG. 8, for example, an outer curved surface of the exterior-cap circular wall 64 includes a knurled pattern 65. As shown in FIG. 1, the exterior-cap circular wall 64 is larger in outer diameter than the neck 15.

The small-inner-diameter portion 68 is connected to the upper end of the large-inner-diameter portion 66. As shown in FIG. 9, the inner surface of the exterior-cap circular wall 64 includes an outer arrangement surface 70 at the boundary between the large-inner-diameter portion 66 and the small-inner-diameter portion 68. The outer arrangement surface 70 perpendicularly intersects the axial direction of the exterior-cap circular wall 64.

The exterior-cap upper wall 72 is connected to the upper end of the exterior-cap circular wall 64. The exterior-cap upper wall 72 has a shape like a disk. The exterior-cap upper wall 72 protrudes outward (leftward in FIG. 9) in the axial direction of the exterior-cap circular wall 64. A label may protrude upward from the top surface of the exterior-cap upper wall 72.

Each of the engaged portions 80 is configured to be engaged with each of the engaging portions 50. The engaged portions 80 are on the outer arrangement surface 70. The engaged portions 80 protrude from the outer arrangement surface 70 to the interior cap 30 (rightward in FIG. 10). The engaged portions 80 are arranged at regular intervals in the circumferential direction of the exterior-cap circular wall 64. The engaged portions 80 is as many as the engaging portions 50.

Each of the engaged portions 80 includes an open-time-pressing-surface 81 and a close-time-pressing-surface 82. Each of the open-time-pressing-surfaces 81 and each of the close-time-pressing-surfaces 82, and the open-time-pressed-surface 51 and the close-time-pressed-surface 52 of the interior cap 30 are described.

The open-time-pressed-surface 51 is pressed by the open-time-pressing-surface 81 of the engaged portion 80 when the exterior-cap main body 62 is rotated in a direction (counterclockwise) to open the exterior-cap main body 62 under a pressed state of the exterior-cap main body 62 pressed against the interior-cap main body 32. The close-time-pressed-surface 52 is pressed by the close-time-pressing-surface 82 of the engaged portion 80 when the pressed exterior-cap main body 62 is rotated in a direction (clockwise) to close the exterior-cap main body 62 under the pressed state. Even when the exterior-cap main body 62 is rotated without being pressed against the interior-cap main body 32, the open-time-pressing-surface 81 or the closetime-pressing-surface 82 does not press the open-time-pressed-surface 51 or the close-time-pressed-surface 52.

An angle defined between each of the open-time-pressed-surfaces 51 and the inner arrangement surface 40 is 90°. An angle defined between each of the close-time-pressed-surfaces 52 and the inner arrangement surface 40 is 90°. An angle defined between each of the open-time-pressing-surfaces 81 and the outer arrangement surface 70 is 90°. An angle defined between each of the close-time-pressing-surfaces 82 and the outer arrangement surface 70 is 90°.

The spring pieces 84 extend from the inner surface of the exterior-cap upper wall 72 to the interior-cap upper wall 42. The spring pieces 84 elastically deform and bend in a direction from the exterior-cap upper wall 72 to the interior-cap upper wall 42. The spring pieces 84 are spirally formed around the central axis of the exterior-cap circular wall 64. The spring pieces 84 urge the exterior-cap main body 62 away from the interior-cap main body 32 to keep the engaged portions 80 away from the engaging portions 50 (the ratchet mechanism disengages) in the unpressed state of the exterior-cap main body 62 which is not pressed against the interior-cap main body 32. When the exterior-cap main body 62 is rotated in a direction (clockwise) to close the mouth 16 with the exterior-cap main body 62 in the unpressed state, the spring pieces 84 engage with the ribs 54 to allow an integral rotation of the interior-cap main body 32 and the exterior-cap main body 62. In detail, the ribs 54 include receiving portions 55 (c.f. FIG. 6) configured to receive the lower ends of the spring pieces 84, respectively when the exterior-cap main body 62 is rotated in a direction (clockwise) to close the mouth 16 with the exterior-cap main body 62 in the unpressed state. The receiving, portions 55 of the ribs 54 are formed to overlap with a circle connecting the proximal ends (upper ends) of the spring pieces 84 in a direction connecting the exterior-cap upper wall 72 with the interior-cap upper wall 42. When the exterior-cap main body 62 is rotated in a direction (counterclockwise) to remove the exterior-cap main body 62 from the mouth 16 in the unpressed state, the spring pieces 84 elastically deform and slide over the ribs 54. In detail, the ribs 54 include guiding portions 56 (c.f. FIG. 6) configured to guide the spring pieces 84, respectively so that the guiding portions 56 allow the spring pieces 84 to slide over the ribs 54 when the exterior-cap main body 62 is rotated in a direction (counterclockwise) to remove the exterior-cap main body 62 from the mouth 16 in the unpressed state.

Next, it is described how to remove the exterior and interior caps 60, 30.

Figure 10:
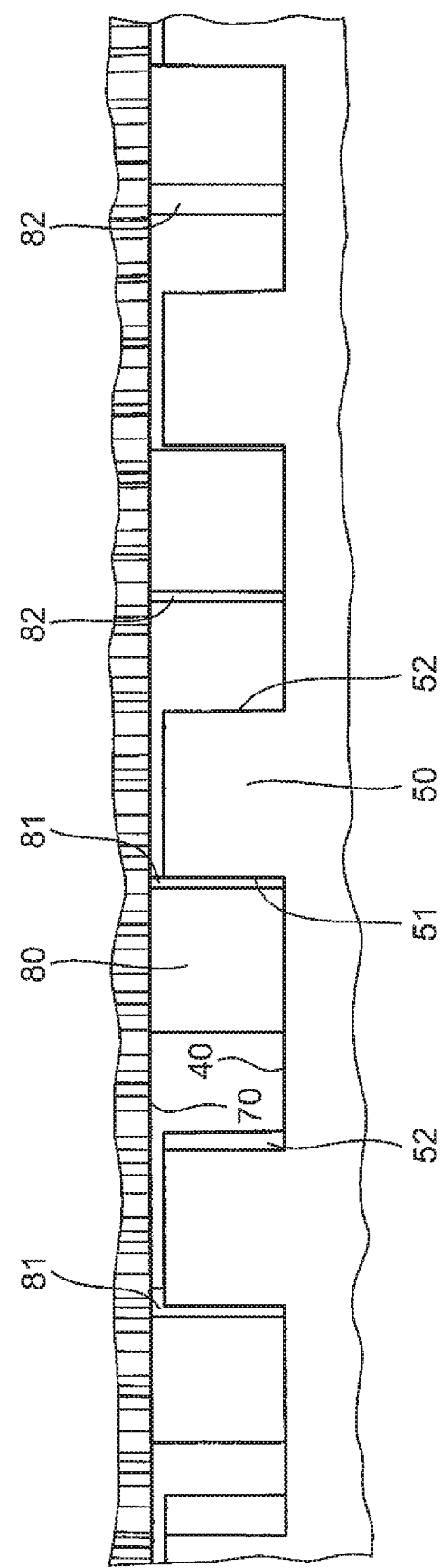
FIG. 10 is a diagram showing an open-time-pressing-surface of engaged portions configured to press an open-time-pressed-surface of engaging portions.

First, the body 13 or the contractive portion 14 is held with one hand whereas the exterior cap 60 is held with the other hand. Then, the exterior cap 60 is pressed to the interior cap 30 (mouth 16) against an urging force of the spring pieces 84. Consequently, the ratchet mechanism is engaged. In detail, the lower ends of the engaged portions 80 come into contact with the inner arrangement surface 40, as shown in FIG. 10. Since the axial direction of the mouth 16 is inclined from the axial direction of the containing portion 11 by the predetermined angle θ in the present embodiment, it is difficult that infants and children press the exterior cap 60 to engage the ratchet mechanism without understanding how to remove the exterior and interior caps 60, 30.

Then, the exterior cap 60 is rotated counterclockwise relative to the mouth 16 in the pressed state of the exterior cap 60 pressed to the interior cap 30 against the urging force of the spring pieces 84 (the engaged state of the ratchet mechanism). Consequently, the exterior and interior caps 60, 30 are rotated counterclockwise relative to the mouth 16 since the open-time-pressing-surfaces 81 of the engaged portions 80 press the respective open-time-pressed-surfaces 51 of the engaging portions 50. Consequently, the caps 30, 60 are removed from the container 10.

On the other hand, even when the exterior cap 60 is rotated counterclockwise without being pressed against the interior cap 30 (without the ratchet mechanism engaging), the open-time-pressing-surfaces 81 do not press the open-time-pressed-surfaces 51, or a sufficient force is not transmitted from the open-time-pressing-surfaces 81 to the open-time-pressed-surfaces 51. Therefore, the exterior cap 60 is rotated relative to the interior cap 30 (i.e. the interior cap 30 does not rotate). Consequently, the caps 60, 30 are not removed from the container 10. At this time, the spring pieces 84 elastically deform and slide over the ribs 54.

In order to attach the caps 60, 30 to the container 10, the exterior cap 60 is rotated in a direction to close the exterior cap 60. In detail, when the exterior cap 60 is rotated in a direction to close the exterior cap 60, the lower ends of the spring pieces 84 presses the receiving portions 55 of the ribs 540 even under the unpressed state. Consequently, rotating the exterior cap 60 in a direction to close the exterior cap 60 results in an integral rotation of the exterior and interior caps 60, 30 relative to the mouth 16. Consequently, when the exterior cap 60 is rotated in a direction to close the exterior cap 60, the exterior and interior caps 60, 30 are attached to the container 10.

As described above, the contact ring 44 is distant from the ribs 54 in the radial direction of the interior-cap circular wall 34, in the present embodiment. In short, the contact ring 44 does not overlap the ribs 54 in the axial direction of the interior-cap circular wall 34. Therefore, the ribs 54 do not cause sink marks on the contact ring 44 when synthetic resin is shaped into the interior cap 30 in a mold. Therefore, the container 10 is tightly sealed.

With regard to the present embodiment, the top surface of the interior-cap upper wall 42 is curved to be convex outward in the axial direction of the interior-cap circular wall 34. Therefore, it is less likely that the engagement weakens with time between the spring pieces 84 and the ribs 54. In detail, since the top surface of the interior-cap upper wall 42 of the present embodiment is curved to be convex toward the exterior-cap main body 62, it is less likely that the interior-cap upper wall 42 dent inwardly even under an inward load continuously acting along the axial direction of the interior-cap circular wall 34, the inward load being transmitted from the spring pieces 84 to the interior-cap upper wall 42. Therefore, it is less likely that the engagement is weakened between the spring pieces 84 and the ribs 54 by the inward load.

The contact ring 44 is distant from the engaging portions 50 in the radial direction of the interior-cap circular wall 34. In short, the contact ring 44 does not overlap the engaging portions 50 in the axial direction of the interior-cap circular wall 34. Therefore, the engaging portions 50 do not cause sink marks on the contact ring 44 when synthetic resin is shaped into the interior cap 30 in a mold.

The aforementioned embodiment is exemplified in all respects and should not be regarded as restrictive. The scope of the present invention is not determined from the aforementioned description of the embodiment, but from the claims. Further, the scope of the present invention includes all variations within the spirit and scope of the claim and the equivalents.

For example, the interior-cap protrusions and the exterior-cap protrusions of the interior and exterior caps 30, 60 may form ribs. However, when the interior-cap protrusions form the ribs 54 like the aforementioned embodiment, it becomes easy to manufacture the interior cap 30. In detail, the interior cap 30 includes the female thread 37. Therefore, when synthetic resin is shaped into the interior cap 30 in a mold, the interior cap 30 has to be rotated to be removed from the mold. In this case, when there are highly protrusive and complicated parts such as the spring pieces, a design of a mold becomes too complicated to allow a rotation of the interior cap 30 for the removal of the interior cap 30 from the mold. Therefore, it becomes more easier to remove the interior cap 30 from a mold when the interior-cap protrusions form ribs 54 than when the interior-cap protrusions form spring pieces.

As shown in FIG. 11, the interior-cap upper wall 42 may have the top surface inside the contact ring 44 in the radial direction of the interior-cap circular wall 34, the top surface perpendicularly intersecting the axial direction of the interior-cap circular wall 34. The interior-cap upper wall 42 may have a bottom surface which is curved to be convex outward in the axial direction of the interior-cap circular wall 34. According to this configuration, the interior-cap upper wall 42 become thick enough inside the contact ring 44. Therefore, the interior-cap upper wall 42 becomes thick enough to prevent sink marks on the contact ring 44 when synthetic resin is shaped into the interior cap 30 in a mold. It is less likely that the interior-cap upper wall 42 dents inwardly under a load transmitted from the spring pieces 84 to the interior-cap upper wall 42. Therefore, it becomes less likely that the engagement is weakened between the spring pieces 84 and the ribs 54 by the inward load.

As shown in FIG. 12, the spring pieces 84 may not be spiral but extend radially from the center of the exterior-cap upper wall 72 (a point of the intersection of the exterior-cap upper wall 72 and the central axis of the exterior-cap circular wall 64). However, when the spring pieces 84 is spirally formed around the central axis of the exterior-cap circular wall 64 like the aforementioned embodiment, a force acting on the proximal ends of the spring pieces 84 is reduced when the exterior-cap main body 62 is pressed against the interior-cap main body 32. Therefore, the spring pieces becomes durable enough. When the spring pieces 84 are spirally formed, the spring pieces is not so hard and gives an appropriate urging force, in comparison to when the spring pieces 84 extend radially from the center of the exterior-cap upper wall 72.

REFERENCE SIGNS 1 medical liquid supply device
10 container
11 containing portion
13 body
15 neck
16 mouth
17 male thread
20 stopper
30 interior cap
32 interior-cap main body
34 interior-cap circular wall
36 large-outer-diameter portion
37 female thread
38 small-outer-diameter portion
40 inner arrangement surface
42 interior-cap upper wall
44 contact ring
50 engaging portion (ratchet mechanism)
51 open-time-pressed-surface
52 close-time-pressed-surface
54 rib (interior-cap protrusion)
60 exterior cap
62 exterior-cap main body
64 exterior-cap circular wall
66 large-inner-diameter portion
68 small-inner-diameter portion
70 outer arrangement surface
72 exterior-cap upper wall
80 engaged portion (ratchet mechanism)
81 open-time-pressing-surface
82 close-time-pressing-surface
82 spring piece exterior-cap protrusion)

The invention claimed is:
1. A liquid medicine supply device comprising:
a container including a tubular containing portion for containing a liquid medicine, and a cylindrical mouth connected to the containing portion, the mouth including a male thread;
an interior cap including an interior-cap circular wall having a female thread with which the male thread of the mouth is engaged, a first portion forming a circular top surface of the interior cap, and a cylindrical second portion extending in an axial direction from a circumferential edge of the first portion and having an outer circumferential surface which is connected to an upper end of the interior-cap circular wall, the interior cap being made of synthetic resin to have a shape operable to block an opening of the mouth; and
an exterior cap attached to an outside of the interior cap, and having a shape operable to cover the interior cap,
a ratchet mechanism including engaging portions integrally formed with an outer surface of the interior-cap circular wall and engaged portions integrally formed with an inner surface of the exterior cap, the engaging portions and the engaged portions being configured to be engaged to allow an integral rotation of the exterior and interior caps when the exterior cap is rotated in a direction to remove the exterior cap from the mouth under a pressed state of the exterior cap pressed against the interior cap whereas the ratchet mechanism allows the exterior cap to be rotated relative to the interior cap when the exterior cap is rotated in a direction to remove the exterior cap from the mouth under an unpressed state of the exterior cap which is not pressed against the interior cap so that the engaged portions are disengaged from the engaging portions,
an interior-cap protrusion protruding from the top surface of the interior cap to the exterior cap,
an annular contact ring protruding from a bottom surface of the second portion to come into contact with the mouth or a stopper attached to the mouth to tightly seal the container,
an exterior-cap protrusion protruding from an inner surface of the exterior cap to the top surface of the interior cap, the exterior-cap protrusion having a shape operable to be engaged with the interior-cap protrusion,
wherein one of the interior-cap protrusion and the exterior-cap protrusion urges the exterior cap away from the interior cap to disengage the engaged portions from the engaging portion under the unpressed state, and
engages with the other of the interior-cap protrusion and the exterior-cap protrusion to allow the integral rotation of the interior cap and the exterior cap when the exterior cap is rotated in a direction to close the mouth with the exterior cap under the unpressed state, wherein one of the interior-cap protrusion and the exterior-cap protrusion elastically deforms and slides over the other protrusion when the exterior cap is rotated in a direction to remove the exterior cap from the mouth under the unpressed state, and wherein the contact ring is distant from the interior-cap protrusion in a radial direction of the interior cap.

2. The liquid medicine supply device according to claim 1, wherein the exterior-cap protrusion forms the one protrusion, the exterior-cap protrusion including spring pieces which extend from the inner surface of the exterior cap to the top surface of the interior cap, and elastically deform and bend in a direction so that the spring pieces connect the inner surface of the exterior cap with the top surface of the interior cap, wherein the interior-cap protrusion forms the other protrusion, the interior-cap protrusion including ribs, each of which has a shape operable to be engaged with lower ends of the spring pieces, and wherein the ribs include:
  receiving portions configured to receive the spring pieces, respectively when the exterior cap is rotated in a direction to close the mouth with the exterior cap under the unpressed state; and
  guiding portions configured to guide the spring pieces, respectively to allow the spring pieces to elastically deform and slide over the ribs when the exterior cap is rotated in a direction to remove the exterior cap from the mouth under the unpressed state.

3. A liquid medicine supply device comprising:
a container including a tubular containing portion for containing a liquid medicine, and a cylindrical mouth connected to the containing portion, the mouth including a male thread;
an interior cap including an interior-cap circular wall having a female thread with which the male thread of the mouth is engaged, and a first portion forming a circular top surface of the interior cap, the interior cap being made of synthetic resin to have a shape operable to block an opening of the mouth; and
an exterior cap attached to an outside of the interior cap, and having a shape operable to cover the interior cap,
a ratchet mechanism including engaging portions integrally formed with an outer surface of the interior-cap circular wall and engaged portions integrally formed with an inner surface of the exterior cap, the engaging portions and the engaged portions being configured to be engaged to allow an integral rotation of the exterior and interior caps when the exterior cap is rotated in a direction to remove the exterior cap from the mouth under a pressed state of the exterior cap pressed against the interior cap whereas the ratchet mechanism allows the exterior cap to be rotated relative to the interior cap when the exterior cap is rotated in a direction to remove the exterior cap from the mouth under an unpressed state of the exterior cap which is not pressed against the interior cap so that the engaged portions are disengaged from the engaging portions,
an interior-cap protrusion protruding from the top surface of the first portion to the exterior cap,
a contact ring which is annular around a central axis of the interior cap and comes into contact with the mouth or a stopper attached to the mouth to tightly seal the container,
an exterior-cap protrusion protruding from an inner surface of the exterior cap to the top surface of the first portion, the exterior-cap protrusion having a shape operable to be engaged with the interior-cap protrusion, wherein the first portion is curved so that the top surface protrudes toward the exterior cap in an axial direction of the interior-cap circular wall, wherein the exterior-cap protrusion applies a force in the axial direction of the interior-cap circular wall to the curved top surface under the pressed state whereas the exterior-cap protrusion supports the exterior cap at a position away from the curved top surface to disengage the engaged portions from the engaging portions under the unpressed state of the exterior cap, wherein the exterior-cap protrusion engages with the interior-cap protrusion to allow the integral rotation of the interior cap and the exterior cap when the exterior cap is rotated in a direction to close the mouth with the exterior cap under the unpressed state, wherein the exterior-cap protrusion elastically deforms and slides over the interior-cap protrusion when the exterior cap is rotated in a direction to remove the exterior cap from the mouth under the unpressed state, and wherein the contact ring is distant from the interior-cap protrusion in a radial direction of the interior can.

4. The liquid medicine supply device according to claim 2, wherein the top surface perpendicularly intersects the axial direction, and wherein the first portion has a bottom surface curved to be convex toward the exterior cap in the axial direction.

5. The liquid medicine supply device according to claim 1, wherein the contact ring is distant from the engaging portions in the radial direction.

6. The liquid medicine supply device according to claim 2, wherein the spring pieces are spirally formed.

7. The liquid medicine supply device according to claim 2, wherein each of ribs is formed on a portion at which each of the ribs overlaps with a circle connecting proximal ends of the spring pieces in a direction connecting the exterior cap with the interior cap.

8. The liquid medicine supply device according to claim 2, wherein the contact ring is distant from the engaging portions in the radial direction.

9. The liquid medicine supply device according to claim 3, wherein the contact ring is distant from the engaging portions in the radial direction.

10. The liquid medicine supply device according to claim 4, wherein the contact ring is distant from the engaging portions in the radial direction.

11. The liquid medicine supply device according to claim 4, wherein the spring pieces are spirally formed.

12. The liquid medicine supply device according to claim 5, wherein the spring pieces are spirally formed.

13. The liquid medicine supply device according to claim 4, wherein each of ribs is formed on a portion at which each of the ribs overlaps with a circle connecting proximal ends of the spring pieces in a direction connecting the exterior cap with the interior cap.

14. The liquid medicine supply device according to claim 5,
wherein each of ribs is formed on a portion at which each of the ribs overlaps with a circle connecting proximal ends of the spring pieces in a direction connecting the exterior cap with the interior cap.

15. The liquid medicine supply device according to claim 6,
wherein each of ribs is formed on a portion at which each of the ribs overlaps with a circle connecting proximal ends of the spring pieces in a direction connecting the exterior cap with the interior cap.

* * * * *